United States Patent [19]

Brunelli et al.

[11] Patent Number: 4,782,191

[45] Date of Patent: * Nov. 1, 1988

[54] PROCESS FOR THE PREPARATION OF ALKYLARYL ETHERS

[75] Inventors: Maurizio Brunelli, San Donato Milanese; Giuseppe Bellussi, Piacenza, both of Italy

[73] Assignee: Eniricerche S.p.A., Milano, Italy

[*] Notice: The portion of the term of this patent subsequent to Mar. 31, 2004 has been disclaimed.

[21] Appl. No.: 50,698

[22] Filed: May 18, 1987

[30] Foreign Application Priority Data

May 27, 1986 [IT] Italy ............................... 20574 A/86

[51] Int. Cl.$^4$ ............................................. C07G 41/09
[52] U.S. Cl. ..................................... 568/630; 568/631
[58] Field of Search ............................... 568/630, 631

[56] References Cited

U.S. PATENT DOCUMENTS

| 4,450,306 | 5/1984 | Eskinazi | 568/630 |
| 4,487,976 | 12/1984 | Farcasiu | 568/630 |
| 4,654,446 | 3/1987 | Brunelli et al. | 568/630 X |

FOREIGN PATENT DOCUMENTS 20574 5/1986 European Pat. Off. ............ 568/630

Primary Examiner—Werren B. Lone
Attorney, Agent, or Firm—Birch, Stewart, Kolasch & Birch

[57] ABSTRACT

Alkylarylethers are produced in accordance with the invention starting from phenols and ethers of aliphatic alcohols in the presence of amorphous $BPO_4$, and calcined at a temperature of from 150° C. to 600° C.

12 Claims, No Drawings

PROCESS FOR THE PREPARATION OF ALKYLARYL ETHERS

The present invention relates to a process for the preparation of alkylarylethers.

More particularly the present invention relates to a process for the preparation of alkylarylethers which comprises reacting phenols with ethers of aliphatic alcohols.

The preparation of alkylarylethers from phenols and ethers of aliphatic alcohols in the presence of strongly acidic ion-exchange resins is known (see European Pat. No. 13924).

The use of ion-exchange resins, however, has a drawback that operating at high temperatures over long periods of time is not possible, in that under such conditions, such resins tend to lose their physical and mechanical characteristics.

Accordingly, it is either necessary to operate at a low temperature which consequently results in a large reduction in yields or, when operating at a high temperature, would result in the necessary frequent replacement of the resin.

An object of the present invention, it has been surprisingly found, that it is possible to replace the strongly acidic resins of the prior art with boron phosphate in its amorphous form.

The process according to the present invention comprises the steps of contacting a phenol or a mixture of phenols with an ether of aliphatic alcohols or a mixture of ethers of aliphatic alcohols, at a temperature of from 150° to 400° C., preferably of from 200° to 300° C., in the presence of amorphous boron phosphate which has been calcined at a temperature of from 150° to 600° C. and of separating the alkylarylether obtained from the other reaction components, by fractionation or crystallization. Example 1 below discloses amorphous boron phosphate in terms of its characteristics and also discloses a method for its preparation. These disclosures are not to be considered as being restrictive of the present invention.

The reaction between phenol or a mixture of phenols and the ether of aliphatic alcohols or the mixture of ethers of aliphatic alcohols can take place in the presence of a solvent or in the absence thereof.

The solvents when used, are hydrocarbons, preferably aromatic hydrocarbons, and particularly toluene.

The amorphous boron phosphate is utilized in amounts by weight in the range of from 0.5% to 50% based on the weight of the reagents.

The process is carried out under atmospheric pressure or higher.

The process can be carried out batchwise or continuously.

In the case of a continuous operation, the catalyst is placed in a fixed or fluid bed in which the reactants are continuously fed through, while the reaction products are continuously withdrawn from the opposite side from which the reagents are introduced.

In the case of a batch operation, at the end of the reaction, the catalyst is removed by filtration of centrifugation, before separating the alkylarylether.

The phenols can be chosen among: phenol, phenols substituted with $C_1$-$C_4$ alkyl groups, such as meta-, ortho-, para-cresol, xylenols and tert-butyl-phenol, phenols substituted with halogen atoms (e.g. ortho-, metha-, para-chlorophenol), polyphenols such as hydroquinone and pyrocatechol, alpha- and beta-naphthol and hydroxyanthracene.

The ethers are chosen among the ethers of aliphatic alcohols having carbon atoms which number in the range of from 1 to 8, preferably from 1 to 4. Particular examples of these ethers are dimethylether, diethylether, dipropylether, diisopropylether, diisobutylether and ditert-butylether.

The following examples are provided to better illustrate the present invention. It is to be understood that the same is not considered to be restricted to or by these examples.

EXAMPLE NO. 1

In a pyrex glass beaker 1000 g distilled water is heated to 70° C. and under stirring, 92.7 g $H_3BO_3$ is added to the heated water.

When all of the $H_3BO_3$ has been dissolved, under constant stirring, 172.8 g of $H_3PO_4$ (85% aqueous solution is added).

The stirring is continued and the water is evaporated until a slurry is obtained.

The solid is dried at 100° C. and a portion thereof is calcined at 170° C. and another portion thereof is calcined at 550° C. for two hours.

The amorphous $BPO_4$ calcined product is then washed 4 times. After each washing, the product is redispersed in one liter of distilled water which is kept boiling, followed by filtering and drying the product.

EXAMPLE NO. 2

Into a 40 ml microreactor, heated by a sand bath and provided with an external system of mechanical stirring, there are charged 10.0 g of amorphous $BPO_4$, prepared as described in Example 1 and calcined at 550° C., 10.0 g of hydroquinone and 14.8 g of dimethyl ether at a weight ratio 1/1/1.48.

The reagents are kept for two hours at the temperature of 280° C. The hydroquinone conversion is 44% by moles, the yield to methyl hydroquinone 33% by moles and the selectivity to methyl hydroquinone 75% by moles.

The gascromatographic analysis of the obtained products gave the following results:

| methyl hydroquinone: | 34.3% by weight |
|---|---|
| dimethyl hydroquinone: | 13.3% by weight |
| hydroquinone: | 52.4% by weight |

EXAMPLE NO. 3

In the same microreactor with the previous procedures there are charged 8.0 g amorphous $BPO_4$ calcined at 170° C., 8.0 g hydroquinone and 7.9 g dimethylether, at a weight ratio 1/1/1. The hydroquinone conversion is 52% by moles, the yield to methyl hydroquinone 45% by moles and the selectivity to methyl hydroquinone 87% by moles. The gas-chromatographic analysis of the products gave the following result:

| methyl hydroquinone: | 47.1% by weight |
|---|---|
| dimethyl hydroquinone: | 7.6% by weight |
| hydroquinone: | 45.3% by weight |

EXAMPLE NO. 4

Into a microreactor, heated by a sand bath and provided with a mechanical stirring system there are charged 10.3 g of amorphous BPO₄ prepared as in example 1 and calcined at 550° C., 10.2 g pyrocatechol and 10,3 g dimethylether at a weight ratio 1/1/1.3.

The reagents are kept for two hours at the temperature of 280° C.

The pyrocatechol conversion is 40%, the yield to guaiacol 37% and the selectivity to guaiacol 92%. The gas-chromatographyc analysis of the obtained products gave the following result:

|  |  |
|---|---|
| guaiacol: | 39.6% by weight |
| veratrole: | 3.4% by weight |
| pyrocatechol: | 57% by weight |

We claim:

1. A process for preparing alkylarlyethers which comprise reacting a phenol or a mixture of phenols with an ether of aliphatic alcohol or a mixture of ethers of aliphatic alcohols, characterized in that the catalyst system is amorphous BPO₄ which has been calcined at a temperature of from 150° to 600° C. and the reaction temperature is selected from a temperature range of from 150° to 400° C.

2. The process of claim 1, characterized in that the selected temperature range is from 200° to 300° C.

3. The process of claim 1, characterized in that the process is carried out in the presence of a hydrocarbon solvent.

4. The process of claim 3, wherein the hydrocarbon solvent is an aromatic solvent.

5. The process of claim 3, wherein the hydrocarbon solvent is toluene.

6. The process of claim 1, wherein the amorphous BPO₄ is present in the amount of 0.5% to 50% by weight based on the weight of the reaction system.

7. The process of claim 1, wherein the phenol or the mixture of phenols is phenol, a $C_1$-$C_4$ alkyl substituted phenol, a halogen substituted phenol, a polyphenol alpha-naphthol, beta-naphthol or hydroxyanthracene.

8. The process of claim 1, wherein the phenol or the mixture of phenols is meta-cresol, ortho-cresol, para-cresol, xylenol or tert-butyl-phenol.

9. The process of claim 1, wherein the phenol or the mixture of phenols is hydroquinone or pyrocatechol.

10. The process of claim 1, wherein the aliphatic alcohol of the ether or ethers has 1 to 8 carbon atoms.

11. The process of claim 10, wherein the aliphatic alcohol has 1 to 4 carbon atoms.

12. The process of claim 1, wherein the ether of aliphatic alcohol or the mixture of ethers of aliphatic alcohols is dimethylether, diethylether, dipropylether, diisopropylether, diisobutylether or ditert-butylether.

* * * * *